US006610326B2

(12) United States Patent
Chen et al.

(10) Patent No.: US 6,610,326 B2
(45) Date of Patent: Aug. 26, 2003

(54) DIVALPROEX SODIUM TABLETS

(75) Inventors: Chih-Ming Chen, Davie, FL (US); Boyong Li, Davie, FL (US)

(73) Assignee: Andrx Corporation, Davie, FL (US)

( * ) Notice: Subject to any disclaimer, the term of this patent is extended or adjusted under 35 U.S.C. 154(b) by 0 days.

(21) Appl. No.: 09/785,069

(22) Filed: Feb. 16, 2001

(65) Prior Publication Data

US 2002/0115718 A1 Aug. 22, 2002

(51) Int. Cl.[7] .............. A61K 9/16; A61K 9/20; A61K 9/22; A61K 9/32; A61K 9/36
(52) U.S. Cl. .......... 424/464; 424/465; 424/468; 424/470; 424/474; 424/475; 424/480; 424/489; 424/490; 424/482
(58) Field of Search ................. 424/465, 464, 424/468, 469, 474, 482, 479, 494, 497, 480, 475, 470, 490, 489

(56) References Cited

U.S. PATENT DOCUMENTS

| | | | |
|---|---|---|---|
| 3,325,361 A | 6/1967 | Meunier et al. | 514/391 |
| 4,558,070 A | 12/1985 | Bauer et al. | 514/557 |
| 4,699,927 A | 10/1987 | Deboeck | 514/564 |
| 4,721,723 A | 1/1988 | Barnes et al. | 514/321 |
| 4,892,739 A | 1/1990 | Shah et al. | 424/473 |
| 4,895,873 A | 1/1990 | Schafer | 514/557 |
| 4,913,906 A | 4/1990 | Friedman et al. | 424/499 |
| 4,957,745 A | 9/1990 | Jonsson et al. | 424/461 |
| 4,988,731 A | 1/1991 | Meade | 514/557 |
| 5,001,161 A | 3/1991 | Appelgren et al. | 514/651 |
| 5,017,613 A | 5/1991 | Aubert et al. | 514/557 |
| 5,049,586 A | 9/1991 | Ortega et al. | 514/557 |
| 5,068,110 A | 11/1991 | Fawzi et al. | 424/461 |
| 5,081,154 A | 1/1992 | Appelgren et al. | 514/651 |
| 5,169,642 A | 12/1992 | Brinker et al. | 424/488 |
| 5,212,326 A | 5/1993 | Meade | 562/606 |
| 5,807,574 A | 9/1998 | Cheskin et al. | 424/451 |
| 5,980,943 A | 11/1999 | Ayer et al. | 424/470 |
| 6,333,352 B1 * | 12/2001 | Derakhshan | 514/557 |

* cited by examiner

Primary Examiner—James M. Spear
(74) Attorney, Agent, or Firm—Davidson, Davidson & Kappel, LLC

(57) ABSTRACT

A process for preparing divalproex sodium tablets is provided. The process comprises preparing a neutralized divalproex sodium solution by combining divalproex sodium, having a sodium valproate and a valproic acid moiety, with an aqueous solvent and a base, e.g., sodium hydroxide, the base being in sufficient amount to ensure neutralization of the valproic acid moiety of the divalproex sodium. The neutralized divalproex sodium solution is sprayed onto a pharmaceutically acceptable carrier, and processed to obtain divalproex sodium tablets.

56 Claims, No Drawings

DIVALPROEX SODIUM TABLETS

FIELD OF THE INVENTION

The present invention is related to a process for formulating divalproex sodium solid oral dosage forms. The process comprises preparing a neutralized divalproex sodium solution, wherein the valproic acid moiety of the divalproex sodium is neutralized by addition of a strong base. The neutralized divalproex sodium solution is subsequently processed into a solid dosage form, such as divalproex sodium tablets.

BACKGROUND OF THE INVENTION

Valproic acid, or 2-propylpentanoic acid, and its salts and derivatives are compounds with anticonvulsant properties. Of these, valproic acid and its sodium salt (sodium valproate) are the most well known. U.S. Pat. No. 3,325,361 describes the use of valproic acid, sodium valproate and other salts and derivatives of valproic acid as anticonvulsants.

It has been recognized by those skilled in the art that both valproic acid and sodium valproate are difficult to formulate into solid oral dosage forms. Valproic acid, for example, is an oily liquid. Sodium valproate is known to be very hygroscopic and to liquify rapidly, and is, therefore, difficult to formulate into tablets.

Efforts have been made to address the problems associated with formulating valproic acid and sodium valproate into solid oral dosage forms. U.S. Pat. No. 5,049,586 (Ortega, et al.) describes valproic acid tablets having a specific composition, which tablets are said to be stable. The tablets contain valproic acid, magnesium oxide, corn starch, poyvinylpyrrolidone, sodium carboxymethylcellulose, and magnesium stearate in specific proportions.

U.S. Pat. No. 5,017,613 (Aubert, et al.) describes a process for preparing a composition containing valproic acid in combination with valproate sodium, wherein the process does not use any binder or granulating solvent. In the process, a mixture of valproic acid and ethylcellulose is prepared and valproate sodium is added to the mixture to form drug granules in the absence of any binder or granulating solvent. Precipitated silica is added to the granules before the compression into tablets.

Efforts have also been made to overcome the limited utility of valproic acid and sodium valproate in formulating solid dosage forms by creating a different salt form or a derivative of valproic acid. U.S. Pat. No. 4,895,873 (Schafer) describes a crystalline calcium salt of valproic acid, in which five valproic acid radicals are associated with one calcium ion. The crystalline salt, called calcium pentavalproate, is said to be non-hygroscopic.

U.S. Pat. No. 4,558,070 (Bauer, et al.) describes potassium, cesium or rubidium salt of valproic acid, which is prepared by combining 4 moles of valproic acid with 1 mole of the potassium, cesium or rubidium. U.S. Pat. No. 4,699,927 (Deboeck) describes arginine, lysine, histidine, ornithine or glycine salts of valproic acid.

U.S. Pat. Nos. 5,212,326 and 4,988,731 (Meade) describe divalproex sodium and its preparation. Divalproex sodium is described as an ionic oligomer in which one mole each of the valproic acid form coordinate bonds with the sodium of the sodium valproate molecule, where the valproate ion is ionically bonded to the sodium ion. Meade also describes the oligomeric compound as having better physical properties than either monomer from which it is made in that the oligomer is a crystalline, non-hygroscopic, stable solid compound.

Some patents describe sustained release dosage forms for divalproex sodium, valproic acid, its salts, amides, or other derivatives. U.S. Pat. No. 5,980,943 (Ayer, et al.) describes a sustained release delivery device for administering divalproex sodium, valproic acid, and its salts and derivatives. The device comprises a semipermeable wall containing drug granules that are microencapsulated with polyalkylene oxide or carboxymethylcellulose polymer.

U.S. Pat. No. 4,913,906 (Friedman, et al.) describes a controlled release dosage form containing divalproex sodium, valproic acid, valpromide and other valproic acid salts and derivatives. The composition is prepared by mixing the drug with hydroxypropyl cellulose, ethylcellulose, or esters of acrylic and methacrylic acid, and by applying high pressure to the mixture of the ingredients.

U.S. Pat. No. 5,807,574 (Cheskin, et al.) describes a controlled release dosage form containing divalproex sodium and a process for its preparation. The process involves melting divalproex sodium and mixing it with a molten wax to form a divalproex sodium-wax composite. The drug-wax mixture is formulated into a capsule.

U.S. Pat. No. 5,169,642 (Brinker, et al.) describes a sustained release dosage form containing granules of divalproex sodium, valproic acid or amides or esters or salts thereof and a polymeric viscosity agent. The drug is coated with a sustained release composition comprising specified portions of ethylcellulose or a methacrylic methylester, plasticizer, and detactifying agent.

U.S. Pat. No. 5,068,110 (Fawzi, et al.) describes various delayed-release tablets and capsules currently marketed, including the delayed-release divalproex sodium tablets manufactured by Abbott Laboratories, and states that the stability of an enteric coated capsules is increased by the application of thicker, higher levels of the enteric coating having a thickness of 14 $mg/cm^2$ to 24 $mg/cm^2$, alone or in combination with a hydroxypropylcellulose, hydroxymethylcellulose or hydroxypropylmethyl cellulose coating.

Divalproex sodium is a oligomer having a 1:1 molar ratio of sodium valproate and valproic acid. The oligomer is described as a stable crystalline solid and is designated as sodium hydrogen bis (2-propyl pentanoate).

Upon administration, divalproex dissociates into valproate ion in the gastrointestinal tract, and in that form exerts its pharmacological effect. Divalproex sodium is indicated for the treatment of patients with complex partial seizures, as well as for the treatment of mania associated with bipolar disorders and for prophylaxis of migraine headaches.

U.S. Pat. No. 4,558,070 (Bauer, et al.) indicates that divalproex sodium is a highly stable, non-hygroscopic, crystalline compound. Bauer also discusses a theory behind the stability of divalproex sodium, stating that it is not a mixture of the two precursors but a chemical entity, and that in the oligomer, the outer shell of electrons of the sodium atom is filled by coordination to the oxygen atoms of both valproic acid and valproate ions, resulting in a stable complex where the sodium ion is completely surrounded by oxygen. Bauer, et al., therefore, appears to indicate that the particular oligomeric structure and the molar ratio of divalproex sodium accounts for the stability of the compound.

Applicants have discovered that divalproex sodium may be formulated into stable solid oral dosage forms, even in the absence of the oligomeric structure and the equimolar ratio of sodium valproate and valproic acid.

OBJECTS AND SUMMARY OF THE INVENTION

It is an object of the invention to provide a process for preparing a divalproex sodium composition.

It is a further object of the invention to provide a process for preparing a divalproex sodium composition, wherein the process comprises preparing a neutralized divalproex sodium solution by combining divalproex sodium, having a valproic acid moiety and a sodium valproate moiety, with a base (e.g., sodium hydroxide) and an aqueous solvent. The base is added in sufficient amount to ensure neutralization of the valproic acid moiety of the divalproex sodium. In the neutralized divalproex sodium solution, divalproex sodium is not present as its oligomeric structure or the 1:1 molar ratio of sodium valproate and valproic acid. The valproic acid of the divalproex sodium is neutralized. Preferably the neutralized divalproex sodium solution contains from about 20 to about 60% valproic acid activity.

It is a further object of the invention to provide an oral solid dosage form containing a therapeutically effective amount of divalproex sodium wherein the divalproex sodium is not present as an oligomeric structure or a 1:1 molar ratio of sodium valproate to valproic acid. It is a further object to provide a new divalproate formulation which provides a delayed release of valproate ion when the dosage form is orally administered to human patients, which dosage form is bioavailable and provides a therapeutic effect which is considered bioequivalent to delayed release divalproex sodium tablets, manufactured by Abbot Laboratories (Depakote®).

The neutralized divalproex sodium solution is sprayed onto a pharmaceutically acceptable carrier, and the resulting mixture may be processed to obtain a divalproex sodium tablet.

In one embodiment of the invention, the pharmaceutically acceptable carrier comprises a plurality of particles of a material such as, for example, anhydrous lactose or microcrystalline cellulose. A granulate is formed by spraying the neutralized divalproex sodium solution onto the carrier. Additional processing steps may then be undertaken to prepare a uniform granulate suitable for formulating into tablets. Sufficient quantities of pharmaceutically necessary tableting excipients may then be admixed with the divalproex granulate, and the resulting mixture may be compressed into tablets.

The divalproex sodium tablets may be coated with an enteric coating to produce delayed-release divalproex sodium tablets. Optionally, a seal coating may also be applied to the tablets before the enteric coating is provided. The enteric coated divalproex sodium tablets may be further overcoated with a film-coating.

In accordance with the invention, the pharmaceutically acceptable carrier may comprise a plurality of inert beads, for example, sugar beads or nonpareil seeds. The neutralized divalproex sodium solution is sprayed onto the inert beads to produce divalproex sodium coated beads, which can then be formulated into solid dosage forms, such as capsules or tablets.

In one embodiment of the invention, the divalproex sodium coated beads may additionally be coated with an enteric coating. In yet another embodiment, a seal coating may be applied to the drug containing beads prior to the application of the enteric coating. After the coatings are applied, the beads may be admixed with sufficient quantities of pharmaceutically necessary tableting excipients. Pharmaceutical tableting excipients include but are not limited to a lubricant, disintegrant, binder, glidant and/or inert diluent. The tablets thus formulated may further be coated with a film-coating.

The invention is further related to a process for preparing divalproex sodium delayed release tablets, wherein the process comprises preparing a neutralized divalproex sodium solution by combining divalproex sodium, having a sodium valproate moiety and a valproic acid moiety, with sodium hydroxide and an aqueous solvent. The base (e.g., sodium hydroxide) is added in sufficient amount to ensure neutralization of the valproic acid moiety of the divalproex sodium. In the neutralized divalproex sodium solution, divalproex sodium does not retain its oligomeric structure or the 1:1 molar ratio of sodium valproate and valproic acid.

The process further comprises spraying the neutralized divalproex sodium solution on a pharmaceutically acceptable carrier and processing the carrier sprayed with the neutralized divalproex sodium solution to obtain divalproex sodium granules. The granules are further processed to obtain divalproex sodium tablet cores, and an enteric coating is applied to the cores to produce divalproex sodium delayed-release tablets. In one example of the invention, a seal coating is applied to the tablet cores prior to the application of the enteric coating. The delayed-release divalproex sodium tablets may also be coated with a film-coating.

In processing the divalproex sodium granules into tablets, as described above, the granules may be admixed with at least one pharmaceutically necessary excipient and compressed into the tablets. Pharmaceutically acceptable excipients include but are not limited to a lubricant, a disintegrant, a binder, a glidant and/or an inert diluent.

The invention is also directed to a method of treating human patients, comprising administering to human patients an effective amounts of the divalproex sodium formulations prepared in accordance with the invention.

The invention is further related to a method of treating complex partial seizures, mania associated with bipolar disorders, and/or migraine headaches in humans comprising orally administering an effective dose of the divalproex sodium formulations prepared in accordance with the invention.

The term "neutralized divalproex sodium," as used in the present invention, refers to divalproex sodium in which the valproic acid moiety has been neutralized by addition of a strong base, e.g., sodium hydroxide. Neutralized divalproex sodium is not an oligomer. Neutralized divalproex sodium also does not exhibit a 1:1 molar ratio of sodium valproate and valproic acid.

Divalproex sodium tablet prepared using neutralized divalproex sodium solution, therefore, does not contain oligomeric divalproex sodium, nor does it exhibit 1:1 molar ratio of sodium valproate and valproic acid.

DETAILED DISCLOSURE OF THE INVENTION

The present invention provides a process for preparing divalproex sodium solid oral dosage forms, where the process comprises preparing a neutralized divalproex sodium solution by combining divalproex sodium with an aqueous solvent and a base, the base added in sufficient quantities to ensure neutralization of the valproic acid moiety of the divalproex sodium. The pH of the neutralized divalproex sodium solution is preferably 10.8±1.0, most preferably ±0.5. In a preferred embodiment, the aqueous solvent is water.

In an embodiment of the invention, the neutralized divalproex sodium solution may be prepared by dissolving divalproex sodium in a basic solution (e.g. sodium hydroxide and water). Additional sodium hydroxide may be added to ensure that the valproic acid moiety of divalproex sodium is neutralized. In a preferred embodiment, additional water is added to the neutralized divalproex sodium solution so that the resulting solution has 20–60%, most preferably 50±3%, valproic acid activity.

In accordance with the present invention, the neutralized divalproex sodium solution is sprayed onto a pharmaceutically acceptable carrier, and the resulting mixture may then be processed to obtain divalproex sodium tablets.

In one embodiment, the pharmaceutically acceptable carrier comprises a plurality of particles of a material that is an inert diluent, and the divalproex sodium solution is sprayed onto the carrier and dried to produce divalproex sodium granules. In another embodiment of the invention, a binder may also be combined with the neutralized divalproex sodium solution and the pharmaceutically acceptable carrier.

In a preferred embodiment of the invention, the neutralized divalproex sodium solution is sprayed onto the pharmaceutically acceptable carrier in a fluid bed processor with a Wurster apparatus. In one embodiment, this process occurs at a product temperature of 42–48° C., with a spray rate of 40–80 ml/min. The divalproex sodium granules may then be dried and then sifted using a mesh screen, e.g., with a 16 mesh screen, to produce divalproex sodium granules.

In a preferred embodiment, the neutralized divalproex sodium solution is diluted, e.g., with isopropyl alcohol before it is sprayed onto the carrier.

The base used in the present invention can be any pharmaceutically acceptable base such as sodium carbonate, sodium bicarbonate, sodium phosphate dibasic, sodium phosphate tribasic, sodium citrate, magnesium hydroxide, magnesium carbonate, calcium carbonate, calcium phosphate, sodium hydroxide and mixtures thereof. A preferred base is sodium hydroxide.

Examples of pharmaceutically acceptable carriers include, but are not limited to, calcium phosphate dihydrate, calcium sulfate dihydrate, microcrystalline cellulose, cellulose derivatives, dextrose, lactose, anhydrous lactose, spray-dried lactose, lactose monohydrate, mannitol, starches, sorbitol and sucrose. Further examples of the carrier include hydroxypropylmethylcellulose, hydroxypropylcellulose, methyl cellulose, carboxymethyl cellulose, sodium carboxymethyl cellulose, polyvinylpyrrolidone, polyethyleneglycol, cellulose acetate butyrate, hydroxyethyl cellulose, ethyl cellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanhydrides, polyvinyl chloride, polyvinyl acetate, ethylene vinyl acetate, lectins, carbopols, silicon elastomers, polyacrylic polymers, maltodextrins, fructose, inositol, trehalose, maltose raffinose, and alpha-, beta-, and gamma-cyclodextrins, and suitable mixtures of the foregoing. A preferred pharmaceutically acceptable carrier is anhydrous lactose.

In certain embodiments, optional pharmaceutical excipients are added to the divalproex sodium granules in the process of formulating the granules into tablets. Such pharmaceutical excipients may include but are not limited to a lubricant, disintegrant, binder, glidant and/or diluent.

Examples of lubricants include magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, and zinc stearate.

Suitable disintegrants include crospovidone, alginates, cellulose and its derivatives, clays, polyvinylpyrrolidone, polysaccharides, such as corn and potato starch, dextrins and sugars. Disintegrants, when used in the formulation, facilitates disintegration when the tablet contacts water in the gastrointestinal tract.

Binders, when added to the formulation, promote granulation and/or promote cohesive compact during the direct compression into tablets. Examples of binders include acacia, cellulose derivatives, gelatin, glucose, polyvinylpyrrolidone, sodium alginate and alginate derivatives, sorbitol, and starch. Binders also include hydrophillic cellulose gums, such as methylcellulose and carboxymethylcellulose, and xanthan gum.

Examples of glidants include but are not limited to corn starch, silica derivatives, and talc.

Examples of inert diluents can include, but are not limited to, calcium phosphate dihydrate, calcium sulfate dihydrate, microcrystalline cellulose, cellulose derivatives, dextrose, lactose, anhydrous lactose, spray-dried lactose, lactose monohydrate, mannitol, starches, sorbitol and sucrose. Further examples of the carrier include hydroxypropylmethylcellulose, hydroxypropylcellulose, methyl cellulose, carboxymethyl cellulose, sodium carboxymethyl cellulose, polyvinylpyrrolidone, polyethyleneglycol, cellulose acetate butyrate, hydroxyethyl cellulose, ethyl cellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanhydrides, polyvinyl chloride, polyvinyl acetate, ethylene vinyl acetate, lectins, carbopols, silicon elastomers, polyacrylic polymers, maltodextrins, fructose, inositol, trehalose, maltose raffinose, and alpha-, beta-, and gamma-cyclodextrins, and suitable mixtures of the foregoing. A preferred pharmaceutically acceptable carrier is anhydrous lactose.

The tablet cores described above may be coated with an enteric coating to obtain delayed-release divalproex sodium tablets that remain intact in the stomach and release the active ingredient in the intestine. Suitable enteric coating may comprise cellulose acetate phthalate, polyvinyl acetate phthalate, acrylic resins such as Eudragit L.RTM., shellac, cellulose acetate butyrate, hydroxypropyl methylcellulose phthalate or combinations thereof.

Additional materials suitable for use in the enteric coating include phthalates including cellulose acetyl phthalate, cellulose triacetyl phthalate, sodium cellulose acetate phthalate, cellulose ester phthalate, cellulose ether phthalate, methylcellulose phthalate, cellulose ester-ether phthalate, hydroxy propyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, and polyvinyl acetate phthalate. The enteric materials are discussed in Remington's Pharmaceutical Sciences, 17th Ed., page 1637 (1985).

The enteric coating may be applied by press coating, molding, spraying, dipping and/or air-suspension or air tumbling procedures. A preferred method of applying the enteric coating is by pan coating, where the enteric coating is applied by spraying the enteric composition onto the tablet cores accompanied by tumbling in a rotating pan. The enteric coating material may be applied to the tablet cores by employing solvents, including an organic, aqueous or a mixture of an organic and aqueous solvent. Examplary solvents suitable in applying the enteric coating include an alcohol, ketone, ester, ether, aliphatic hydrocarbon, halogenated solvents, cycloaliphatic solvents, aromatic, heterocyclic, aqueous solvents, and mixtures thereof. In a preferred embodiment, the enteric coating comprises cellacefate and diethyl phthalate in isopropyl alcohol and acetone. In preferred embodiments, the coating has a thickness from about 6% to about 8% of the final dosage form.

In accordance with the invention, the divalproex sodium tablet cores may further be coated with a seal coating. In a preferred embodiment, the seal coating occurs between the tablet core and the enteric coating. The seal coating may comprise a hydrophilic polymer. Examples include but are not limited to hydroxypropyl cellulose, hydroxypropylmethylcellulose, methoxypropyl cellulose, hydroxypropylisopropylcellulose, hydroxypropylpentylcellulose, hydroxypropylhexylcellulose and any mixtures thereof.

The seal coating, like the enteric coating, may be applied by press coating, molding, spraying, dipping and/or air-suspension or air tumbling procedures. A preferred method of applying the seal coating is by pan coating, where the seal coating is applied by spraying it onto the tablet cores accompanied by tumbling in a rotating pan. The seal coating material may be applied to the tablets as a suspension by employing solvents, e.g., an organic, aqueous, or a mixture of an organic and aqueous solvent. Examplary solvents suitable in applying the seal coating include aqueous-based solutions, an alcohol, ketone, ester, ether, aliphatic hydrocarbon, halogenated solvents, cycloaliphatic solvents, aromatic, heterocyclic, aqueous solvents, and mixtures thereof. In a preferred embodiment, the seal coating comprises hydroxypropyl cellulose and hydroxypropylmethylcellulose, and is delivered as a suspension using ethanol as a solvent.

The divalproex sodium tablets may be overcoated with a pharmaceutically acceptable film coating, e.g., for aesthetic purposes (e.g., including a colorant), for stability purposes (e.g., coated with a moisture barrier), for taste-masking purposes, etc. For example, the tablets may be overcoated with a film coating, preferably containing a pigment and a barrier agent, such as hydroxypropylmethycellulose and/or a polymethylmethacrylate. An example of a suitable material which may be used for such overcoating is hydroxypropylmethylcellulose (e.g., Opadry®, commercially available from Colorcon, West Point, Pa.). In a preferred embodiment, an overcoating is applied to the divalproex sodium tablets that have already been coated with a seal coating and an enteric coating. The overcoat may be applied using a coating pan or a fluidized bed, and may be applied by using a solvent, preferably an aqueous solvent.

The final product is optionally subjected to a polishing step to improve the appearance of the final product and also to facilitate the manipulation of the formulation post manufacture. For example, the slippery nature of the polished dosage form aids in filling printer carrier bars with the formulation and facilitates final packaging of the product. Suitable polishing agents are polyethylene glycols of differing molecular weight or mixtures thereof, talc, surfactants (e.g., Brij types, Myrj types, glycerol mono-stearate and poloxamers), fatty alcohols (e.g., stearyl alcohol, cetyl alcohol, lauryl alcohol and myristyl alcohol) and waxes (e.g., carnauba wax, candelilla wax and white wax). Preferably, polyethylene glycols having molecular weight of 3,000–20,000 are employed.

In certain embodiments of the present invention, the pharmaceutically acceptable carrier onto which the neutralized divalproex sodium solution is sprayed comprises a plurality of inert beads, e.g., sugar beads. The divalproex sodium coated beads thus obtained may be coated with an enteric coating. The beads may also be coated with a seal coating, preferably the seal coating being applied before the enteric coating. The suitable enteric coating and the seal coating materials are set forth above.

The divalproex sodium beads may be formulated into solid oral dosage forms. For example, the beads made be formulated into tablets by admixing them with sufficient quantities of a pharmaceutically necessary tableting excipient and compressing the resulting mixture. The pharmaceutically necessary tableting excipient is selected from the group consisting of a lubricant, a disintegrant, a binder, a glidant, an inert diluent and mixtures thereof. Suitable tableting excipients are set forth above.

In certain preferred embodiments, the present invention provides a process for preparing divalproex sodium delayed-release tablets. The process comprises preparing a neutralized divalproex sodium solution by combining divalproex sodium, having a sodium valproate moiety and a valproic acid moiety, with an aqueous solvent and a base, e.g., sodium hydroxide, the bases being added in sufficient amount to ensure neutralization of the valproic acid moiety of the divalproex sodium. The process further comprises spraying the neutralized divalproex sodium solution onto a pharmaceutically acceptable diluent, processing the resulting mixture to obtain divalproex sodium granules, and processing the granules to obtain tablet cores. An enteric coating is applied to the divalproex sodium tablet cores to produce divalproex sodium delayed-release tablets. Preferably, the delayed-release tablet further comprises a seal coating, applied between the core and the enteric coating. Suitable material for the seal coating and the enteric coating, as well as the procedures for application of these coatings, are set forth above. The tablet thus produced does not contain divalproex sodium that is an oligomeric compound and does not have a 1:1 molar ratio of sodium valproate and valproic acid. Rather, the tablets of the present invention contain divalproex sodium in which the valproic acid moiety has been neutralized.

The pH of the neutralized divalproex sodium solution is preferably about 10.8±0.5, and the neutralized divalproex sodium solution preferably has about 50±3% valproic acid activity. A preferred aqueous solvent for preparation of the neutralized divalproex sodium solution is water.

In a preferred embodiment, the processing of the divalproex sodium granules to obtain tablets comprises drying and then screening the divalproex sodium granules, and admixing the screened divalproex sodium granules with pharmaceutically necessary excipients and compressing the resulting mixture into tablets. The pharmaceutically acceptable excipients are selected from the group consisting of a lubricant, a disintegrant, a binder, a glidant, an inert diluent and mixtures thereof. Examples of suitable excipients are listed above.

In a preferred embodiment, the neutralized divalproex sodium solution is diluted with isopropyl alcohol before it is sprayed onto anhydrous lactose in a fluid bed processor with a Wurster apparatus at product temperature of, e.g., 42–48° C. and a spray rate of, e.g., 40–80 ml/min to form granules. The granules are sized through an appropriate sized screen, e.g., a 16 mesh screen. The sized granules are blended with crospovidone, anhydrous lactose, colloidal silicon dioxide and magnesium stearate and compressed into tablets. The tablets are coated with a seal coating in a coating pan with a suspension of hydroxypropylmethylcellulose, hydroxypropylethylcellulose, hydroxypropyl cellulose and magnesium stearate in ethanol. An enteric coating is then applied, also in a coating pan. The enteric coating comprises cellacefate and diethyl phthalate in isopropyl alcohol and acetone. As an optional final step, the enteric coated tablet is film coated and subjected to a polishing step.

DETAILED DESCRIPTION OF THE PREFERRED EMBODIMENTS

The following example illustrate various aspects of the present invention. It is not to be construed to limit the claims in any manner whatsoever.

EXAMPLE 1

Divalproex Sodium Delayed Release Tablets

1. Preparation of Neutralized Divalproex Sodium Solution

Neutralized divalproex sodium solution is prepared by dissolving 260 kg of divalproex sodium in about 189.49 kg purified water with 33.51 kg of sodium hydroxide. The solution is adjusted to pH 10.8±0.3 with 20% sodium hydroxide solution and adjusted to 483 kg with additional purified water to yield divalproex sodium solution with 50±3% valproic acid activity.

2. Preparation Divalproex Sodium Granules 11.52 kg of the neutralized divalproex sodium solution is diluted with 14.57 kg of isopropyl alcohol. The diluted solution is then sprayed onto 5.15 kg anhydrous lactose in a fluid bed processor with a Wurster apparatus at product temperature of 42–48° C. and spray rate of 40–80 ml/min to form divalproex sodium granules. The granules are sized through a sifter equipped with 16 mesh screen.

3. Blending and Tableting

The sifted divalproex sodium granules, 102.51 kg, are blended with 3.987 kg crospovidone, 5.695 kg anhydrous lactose, 0.57 kg colloidal silicon dioxide and 1.139 magnesium stearate to yield divalproex sodium blend. The divalproex sodium blend is then compressed to yield divalproex sodium tablets having a weight of 871 to 983 mg, with 500 mg valproic acid activity.

4. Seal Coating and Enteric Coating

The divalproex sodium tablet cores, 108.3 kg, are seal coated in a coating pan with a suspension of 1.34 kg hydroxypropylmethylcellulose, 1.34 kg hydroxypropylcellulose and 0.67 kg magnesium stearate in 30.15 kg ethanol. The seal coated tablets, 110.71 kg, are coated in a coating pan with a solution of 7.181 kg cellacefate (CAP) and 1.795 kg diethyl phthalate in 31.42 kg ispropyl alcohol and 31.42 kg acetone to yield enteric coated, delayed-release divalproex sodium tablets.

5. Color Coating and Polishing

The enteric coated tablets, 118.51 kg, are color coated with a solution of 3.291 kg Opadry Blue and 0.037 kg Vanillin in 29.62 kg water. The color coated tablets are then polished by sprinkling 0.037 kg candelilla wax powder onto the tablets while the pan is rotating to yield color-coated divalproex sodium delayed-release tablets, with 500 mg valproic acid activity.

The example provided above is not meant to be exclusive. Many other variations of the present invention would be obvious to those skilled in the art, and are contemplated to be within the scope of the appended claims. For example, it will be recognized by those skilled in the art that a wide variety of pharmaceutically acceptable excipients may be utilized for their intended purpose in the process for preparing divalproex sodium tablets as described herein.

EXAMPLES 2–10

In Example 2, divalproex delayed release tablets were prepared in accordance with Example 1, with an equivalent amount of sodium carbonate substituted for the sodium hydroxide.

In Example 3, divalproex delayed release tablets were prepared in accordance with Example 1, with an equivalent amount of sodium bicarbonate substituted for the sodium hydroxide.

In Example 4, divalproex delayed release tablets were prepared in accordance with Example 1, with an equivalent amount of sodium phosphate dibasic substituted for the sodium hydroxide.

In Example 5, divalproex delayed release tablets were prepared in accordance with Example 1, with an equivalent amount of sodium phosphate tribasic substituted for the sodium hydroxide.

In Example 6, divalproex delayed release tablets were prepared in accordance with Example 1, with an equivalent amount of sodium citrate substituted for the sodium hydroxide.

In Example 7, divalproex delayed release tablets were prepared in accordance with Example 1, with an equivalent amount of magnesium hydroxide substituted for the sodium hydroxide.

In Example 8, divalproex delayed release tablets were prepared in accordance with Example 1, with an equivalent amount of magnesium carbonate substituted for the sodium hydroxide.

In Example 9, divalproex delayed release tablets were prepared in accordance with Example 1, with an equivalent amount of calcium carbonate substituted for the sodium hydroxide.

In Example 10, divalproex delayed release tablets were prepared in accordance with Example 1, with an equivalent amount of calcium phosphate substituted for the sodium hydroxide.

What is claimed is:

1. A pharmaceutical formulation comprising a therapeutically effective dose of neutralized divalproex sodium and a pharmaceutically acceptable carrier.

2. The pharmaceutical formulation of claim 1 wherein said carrier is selected from the group consisting of calcium phosphate dihydrate, calcium sulfate dihydrate, microcrystalline cellulose, cellulose derivatives, dextrose, lactose, anhydrous lactose, spray-dried lactose, lactose monohydrate, mannitol, starches, sorbitol, sucrose, hydroxypropylmethylcellulose, hydroxypropylcellulose, methyl cellulose, carboxymethyl cellulose, sodium carboxymethyl cellulose, polyvinylpyrrolidone, polyethyleneglycol, cellulose acetate butyrate, hydroxyethyl cellulose, ethyl cellulose, polyvinyl alcohol, polypropylene, dextrans, dextrins, hydroxypropyl-beta-cyclodextrin, chitosan, copolymers of lactic and glycolic acid, lactic acid polymers, glycolic acid polymers, polyorthoesters, polyanyhydrides, polyvinyl chloride, polyvinyl acetate, ethylene vinyl acetate, lectins, carbopols, silicon elastomers, polyacrylic polymers, maltodextrins, fructose, inositol, trehalose, maltose raffinose, alpha-, beta-, and gamma-cyclodextrins, and suitable mixtures of the foregoing.

3. The pharmaceutical formulation of claim 2 wherein said carrier is anhydrous lactose.

4. The pharmaceutical formulation of claim 1 wherein said therapeutically effective dose of neutralized divalproex sodium and said pharmaceutically acceptable carrier is compressed into a tablet.

5. The pharmaceutical composition of claim 1 wherein the pharmaceutically acceptable carrier comprises a plurality of inert beads.

6. The pharmaceutical composition of claim 5, wherein the neutralized divalproex sodium is coated onto said inert beads.

7. The pharmaceutical composition of claim 6, wherein said coated beads are admixing with a sufficient quantity of pharmaceutically acceptable tableting excipients and compressed into a tablet.

8. The pharmaceutical composition of claim 7, wherein said pharmaceutically acceptable tableting excipients are selected from the group consisting of a lubricant, a disintegrant, a binder, a glidant, an inert diluent and mixtures thereof.

9. The composition of claim 4, further comprising an enteric coating applied to the tablet.

10. The composition of claim 9, further comprising a seal coating between the tablet and the enteric coating.

11. The composition of claim 9, further comprising a film coating applied to the enteric coated tablet.

12. The composition of claim 7, further comprising an enteric coating applied to the tablet.

13. The composition of claim 12, further comprising a seal coating between the tablet and the enteric coating.

14. The composition of claim 12, further comprising a film coating applied to the enteric coated tablet.

15. A process for preparing an orally administrable divalproex sodium formulation, which comprises
   (a) preparing a neutralized divalproex sodium solution by combining divalproex sodium, having a sodium valproate moiety and a valproic acid moiety, with a base and an aqueous solvent, the base being added in sufficient amount to ensure neutralization of the valproic acid moiety of the divalproex sodium, and
   (b) spraying the neutralized divalproex sodium solution onto a pharmaceutically acceptable carrier.

16. The process of claim 15 wherein said base is selected from the group consisting of sodium carbonate, sodium bicarbonate, sodium phosphate dibasic, sodium phosphate tribasic, sodium citrate, magnesium hydroxide, magnesium carbonate, calcium carbonate, calcium phosphate, sodium hydroxide and mixtures thereof.

17. The process of claim 15 wherein said base is sodium hydroxide.

18. The process of claim 15, wherein the pharmaceutically acceptable carrier sprayed with the neutralized divalproex sodium is processed to obtain a divalproex sodium tablet core.

19. The process of claim 18, wherein an enteric coating is applied to the tablet core.

20. The process of claim 15, wherein the pH of the neutralized divalproex sodium solution is about 10.8±1.

21. The process of claim 15, wherein the neutralized divalproex sodium solution contains from about 20 to about 60% valproic acid activity.

22. The process of claim 15, wherein the aqueous solvent is water.

23. The process of claim 15, wherein the pharmaceutically acceptable carrier sprayed with the neutralized divalproex sodium is processed to obtain divalproex sodium granules.

24. The process of claim 23, further comprising admixing said divalproex sodium granules with sufficient quantities of pharmaceutically necessary tableting excipients and compressing said mixture into a tablet core.

25. The process of claim 24, wherein the pharmaceutically necessary tableting excipient is selected from the group consisting of a lubricant, a disintegrant, a binder, a glidant, an inert diluent and mixtures thereof.

26. The process of claim 23, wherein prior to admixing with the pharmaceutically necessary tablet excipients, the granules are dried to evaporate any excess solvent, and thereafter screened to obtain uniformly sized particles.

27. The process of claim 18, further comprising coating the divalproex sodium tablets with a seal coating.

28. The process of claim 27, wherein an enteric coating is provided over the seal coating.

29. The process of claim 27, wherein a further seal coating is provided over the enteric coating.

30. The process of claim 19, wherein the pharmaceutically acceptable carrier comprises anhydrous lactose.

31. The process of claim 19, wherein the enteric coating is selected from the group consisting of methacrylic acid-methacrylic ester copolymer, cellulose acetate phthalate, a polyvinyl acetate phthalate, diethyl phthalate and mixtures thereof.

32. The process of claim 27, wherein the seal coating is selected from the group consisting of hydroxylpropylmethylcellulose, hydroxypropylcellulose, hydroxypropylethylcellulose and mixtures thereof.

33. The process of claim 19, further comprising applying a film coat to the enteric coated tablet core.

34. The process of claim 15, wherein the pharmaceutically acceptable carrier comprises a plurality of inert beads, and the inert beads are sprayed with the neutralized divalproex sodium solution to obtain divalproex sodium coated beads.

35. The further process of claim 34, wherein the divalproex sodium coated beads are further coated with an enteric coating.

36. The process of claim 35, further comprising applying a seal coating to the divalproex sodium coated beads, wherein the seal coating is provided between the divalproex sodium beads and the enteric coating.

37. The process of claim 34, wherein the tablet is formulated by admixing divalproex sodium beads with sufficient quantities of pharmaceutically necessary tableting excipients and compressing said mixture to produce the tablet.

38. The process of claim 37, wherein the pharmaceutically necessary tableting excipient is selected from the group consisting of a lubricant, a disintegrant, a binder, a glidant, an inert diluent and mixtures thereof.

39. A process for preparing a divalproex sodium tablet, which comprises
   a) preparing a neutralized divalproex sodium solution by combining divalproex sodium, having a sodium valproate moiety and a valproic acid moiety, with a base and an aqueous solvent, the base being added in sufficient amount to ensure neutralization of the valproic acid moiety of the divalproex sodium;
   b) spraying the neutralized divalproex sodium solution onto a pharmaceutically acceptable carrier;
   c) processing the pharmaceutically acceptable carrier sprayed with the neutralized divalproex sodium solution to obtain divalproex sodium granules;
   d) compressing said divalproex sodium granules together with effective amounts optional pharmaceutical excipients to obtain a divalproex sodium tablet containing a therapeutically effective amount of valproate ions;
   e) processing the divalproex sodium granules to obtain a tablet core; and
   f) applying an enteric coating to the divalproex sodium tablet core to produce a divalproex sodium delayed-release tablet.

40. The process of claim 39 wherein said base is selected from the group consisting of sodium carbonate, sodium bicarbonate, sodium phosphate dibasic, sodium phosphate tribasic, sodium citrate, magnesium hydroxide, magnesium carbonate, calcium carbonate, calcium phosphate, sodium hydroxide and mixtures thereof.

41. The process of claim 39 wherein said base is sodium hydroxide.

42. The process of claim 39, wherein the pH of the neutralized divalproex sodium solution is about 10.8±0.5, and the neutralized divalproex sodium solution contains 50±3% valproic acid activity.

43. The process of claim 39, wherein the processing of the divalproex sodium granules to obtain the tablet comprises drying and then screening the divalproex sodium granules, and admixing the screened divalproex sodium granules with a pharmaceutically necessary excipient and compressing the resulting mixture into the tablet.

44. The process of claim 43, wherein the pharmaceutically acceptable excipient is selected from the group consisting of a lubricant, a disintegrant, a binder, a glidant, an inert diluent, and mixtures thereof.

45. The process of claim 43, further comprising the step of applying a seal coating to the divalproex sodium tablet core before the enteric coating is applied.

46. A process for preparing an orally administrable divalproex sodium formulation, which comprises (a) preparing a neutralized divalproex sodium solution by combining divalproex sodium, having a sodium valproate moiety and a valproic acid moiety, with a base and an aqueous solvent, the base being added in sufficient amount to ensure neutralization of the valproic acid moiety of the divalproex sodium, and (b) spraying the neutralized divalproex sodium solution onto a plurality of inert beads, and the inert beads to obtain neutralized divalproex sodium coated beads, (c) compressing an effective amount of said neutralized divalproex sodium coated beads to form a tablet; and (d) coating said tablet with at least one coating layer comprising an enteric polymer to form an enteric coated tablet.

47. The process of claim 46 wherein said base is selected from the group consisting of sodium carbonate, sodium bicarbonate, sodium phosphate dibasic, sodium phosphate tribasic, sodium citrate, magnesium hydroxide, magnesium carbonate, calcium carbonate, calcium phosphate, sodium hydroxide and mixtures thereof.

48. The process of claim 46 wherein said base is sodium hydroxide.

49. The process of claim 46 wherein said neutralized divalproex sodium coated beads are admixed with pharmaceutically acceptable excipients prior to compression to form said tablet.

50. The process of claim 46 wherein said tablet is seal coated before the coating with the enteric layer.

51. The process of claim 46 wherein said enteric coated tablet is coated with a further seal coating.

52. The process of claim 46 wherein said neutralized divalproex sodium coated beads are enteric coated prior to compression to form said tablet.

53. The product obtained by the process of claim 15.

54. The product obtained by the process of claim 39.

55. The product obtained by the process of claim 46.

56. A method of treating complex seizures, mania associated with bipolar disorders or migraine comprising administering a formulation according to claim 1.

* * * * *